United States Patent [19]

Amen et al.

[11] Patent Number: 4,797,364

[45] Date of Patent: Jan. 10, 1989

[54] PROCESS FOR PREPARING CONCENTRATED AMOUNTS OF LYOPHILIZED MICROORGANISMS

[75] Inventors: Jean Amen, Versailles; Michel Cabau, Coublevie Voiron, both of France

[73] Assignee: l'Air Liquide, Societe Anonyme pour l'Etude et l'Exploitation des Procedes Georges Claude, Paris, France

[21] Appl. No.: 46,261

[22] Filed: May 5, 1987

Related U.S. Application Data

[63] Continuation-in-part of Ser. No. 663,986, Oct. 23, 1984, abandoned.

[30] Foreign Application Priority Data

Oct. 27, 1983 [FR] France ................... 83 17156

[51] Int. Cl.$^4$ ................... C12N 1/00; C12N 1/02
[52] U.S. Cl. ................... 435/243; 435/260; 435/261; 435/853; 435/252.1; 435/252.4; 435/252.9
[58] Field of Search ............ 435/240.1, 240.2, 240.31, 435/240.4, 240.54, 243, 260, 261, 853, 253

[56] References Cited

U.S. PATENT DOCUMENTS 3,911,140 10/1975 Osborne et al.
4,018,593 4/1977 Müller ................... 435/803
4,382,965 5/1983 Sandine et al. ................... 435/139

FOREIGN PATENT DOCUMENTS 0065895 12/1982 European Pat. Off.
2813714 10/1979 Fed. Rep. of Germany.
2126452 10/1972 France.

*Primary Examiner*—Margaret Moskowitz
*Attorney, Agent, or Firm*—Young & Thompson

[57] ABSTRACT

The process for preparing concentrated amounts of lyophilized micro-organisms employs an ultrafiltration with a supply of nutritive substrates and the supply of a neutralizing agent in the fermenter, and further comprises the following steps:

(a) ceasing to supply substrates while cooling;
(b) continuing the ultrafiltration until the obtainment of a primary concentrate (40–80 kg dry weight of bacteria/cu. m) and cooling to 15°–20° C.;
(c) washing the primary concentrate with mineral salts and amino acids, oligo-elements and vitamins;
(d) concentrating by ultrafiltration to 90–220 kg dry weight of bacteria/cu. m;
(e) cooling to 5° C. and adding a protector;
(f) deep freezing and lyophilizing.

The process particularly applies to the preparation of lactic bacteria.

11 Claims, No Drawings

PROCESS FOR PREPARING CONCENTRATED AMOUNTS OF LYOPHILIZED MICROORGANISMS

This application is a continuation-in-part of application Ser. No. 663,986, filed 10/23/84, abandoned.

The present invention relates to a process for preparing concentrated amounts of lyophilized microorganisms, in particular lactic bacteria, of the type comprising feeding a culture medium which was previously seeded and maintained at a temperature between 25° C. and 45° C., and preferably on the order of 30° C., with a nutritive substrate comprising lactose and yeast, and a neutralizing agent, in particular ammonia or sodium, for maintaining the pH of the culture medium at a constant value between 5.5 and 7.5, and in particular between 6 and 7, the whole being diluted in water, adjusting the supplies of substrate and water relative to the neutralizing agent by a continuous determination of the concentration of inhibiting agent, so as to ensure in a first stage a high growth rate until to attaining a critical concentration of inhibiting agent, which corresponds to a maximum permissible concentration for a more moderate growth rate between 0.10 and 0.50/hr chosen for a subsequent growth stage, and effecting an ultrafiltration operation for partially eliminating the inhibiting agent while maintaining a constant volume of the culture medium. The inhibiting agent is generated by the microorganisms during growth, and retards subsequent growth as a function of its concentration. In the case of lactic bacteria, the inhibiting agent may be lactic acid, lactate, D-leucine and/or hydrogen peroxide.

An object of the invention is to specify the essential conditions of the operations which follow that of the culture and which ensure an optimum lyophilization.

According to the invention the process comprises the following operations:

(a) Ceasing the supply of nutritive substrate and water, while maintaining the pH at said constant value by supplying neutralizing agent and, (b) continuing the ultrafiltration operation simultaneously with a cooling so as to ensure a primary concentration of microorganisms between 40 and 80 kg of dry weight of bacteria per cubic meter at a temperature between 15° C. and 20° C. and preferably on the order of 16° C.;

(c) proceeding to the washing of the primary concentrate, by means of a washing solution formed by a mixture of mineral salts and amino acids, oligo-elements and vitamins;

(d) ensuring by ultrafiltration a final concentration between 90 and 220 kg dry weight of bacteria/cu. m while maintaining the temperature such as indicated at (b);

(e) cooling the bacterial concentrate to a temperature on the order of 5° C. and adding a concentrated protector thereto;

(f) proceeding to a deep freezing of the bacterial concentrate and to its lyophilization.

By way of example the composition of the washing solution may be chosen from those listed below:

EXAMPLE 1

| | |
|---|---|
| E. yeast | 15–25 g/l |
| $KH_2 PO_4$ | 3–5 g/l |
| $Na_2H PO_4$, 12 $H_2O$ | 20–30 g/l |
| $MgSO_4$, 7$H_2O$ | 0.3–0.8 g/l |

EXAMPLE 2

| | |
|---|---|
| E. yeast | 1–3 g/l |
| $KH_2 PO_4$ | 1–4 g/l |
| $Na_2H PO_4$, 12 $H_2O$ | 7–13 g/l |
| $MgSO_3$, 7$H_2O$ | 0.3–0.6 g/l |
| NaCl | 8–12 g/l |

EXAMPLE 3

| | |
|---|---|
| E. yeast | 1–3 g/l |
| $KH_2 PO_4$ | 1–2 g/l |
| $Na_2H PO_4$, 12 $H_2O$ | 4–8 g/l |
| $MgSO_4$, 7$H_2O$ | 0.3–0.6 g/l |
| NaCl | 8–12 g/l |
| Glycerophosphate Na | 3–8 g/l |

EXAMPLE 4

| | |
|---|---|
| E. yeast | 1–3 g/l |
| $KH_2 PO_4$ | 1–2 g/l |
| $Na_2H PO_4$, 12 $H_2O$ | 4–8 g/l |
| $MgSO_4$, 7$H_2O$ | 0.3–0.6 g/l |
| NaCl | 6–10 g/l |
| Glycerophosphate Na | 3–8 g/l |
| Glutamate Na | 2–5 g/l |

EXAMPLE 5

| | |
|---|---|
| E. yeast | 1–3 g/l |
| $KH_2 PO_4$ | 1–2 g/l |
| $Na_2 PO_4$, 12 $H_2O$ | 4–8 g/l |
| $MgSO_4$, 7$H_2O$ | 0.3–0.6 g/l |
| NaCl | 5–9 g/l |
| Glycerophosphate Na | 3–8 g/l |
| Glutamate Na | 2–5 g/l |
| Sodium ascorbate | 2–5 g/l |

All of these steps employ in succession a maintenance of a constant pH of between 5.5 and 7.5 and more particularly 6 and 7, specific cooling and primary concentration, then a washing and a final concentration so as to ensure, as only experience will show, a perfect lyophilization of the microorganisms and in particular of the lactic bacteria.

We claim:

1. In a process for preparing microorganisms, of the type comprising the steps of: supplying a culture medium, which was previously seeded and maintained at a temperature of between 25° C. and 45° C. with a nutritive substrate comprising lactose and yeast, a neutralizing agent selected to maintain the pH of the culture medium at a constant value between 5.5 and 7.5, the whole being diluted in water; adjusting the supplies of substrate and water relative to the neutralizing agent based on a determination of the concentration of inhibiting agent generated by the microorganisms, said inhibiting agent retarding the subsequent growth of microorganisms as a function of its concentration; and effecting an ultrafiltration operation for reducing the quantity of said inhibiting agent while maintaining a constant volume of the culture medium, the improvement comprising the steps of:
- (a) ceasing the supply of nutritive substrate and water, while maintaining the pH at said constant value by supplying said neutralizing agent;
- (b) continuing the ultrafiltration operation simultaneously with cooling at a temperature between 15° C. and 20° C. to obtain a primary concentration of microorganisms between 40 and 80 kg dry weight of microorganisms per cubic meter;
- (c) washing said primary concentration with a washing solution comprising mineral salts and amino acids;
- (d) ultrafiltering said washed primary concentration to a final concentration between 90 and 220 kg dry weight of microorganisms/cubic meter;
- (e) cooling the said final concentration to a temperature of 5° C.; and
- (f) lyophilizing said final concentration.

2. A process for preparing micro-organisms according to claim 1, wherein the culture medium is maintained at a temperature of 30° C. during said supplying.

3. A process for preparing micro-organisms according to claim 1, wherein the neutralizing agent is selected from the group consisting of ammonia and sodium.

4. A process for preparing micro-organisms according to claim 1, wherein the pH of the culture medium is maintained at a constant value between 6 and 7.

5. A process for preparing micro-organisms according to claim 1, wherein the step of continuing the ultrafiltration operation simultaneously with a cooling is performed at a temperature of 16° C.

6. A process for preparing micro-organisms according to claim 1, wherein the washing solution comprises a yeast extract, $KH_2PO_4$, $Na_2HPO_4.12H_2O$, and $MgSO_4.7H_2O$.

7. A process for producing micro-organisms according to claim 6, wherein the washing solution comprises NaCl.

8. A process for producing micro-organisms according to claim 7, wherein the washing solution comprises sodium glycerophosphate.

9. A process for producing micro-organisms according to claim 8, wherein the washing solution comprises sodium glutomate.

10. A process for producing micro-organisms according to claim 9, wherein the washing solution comprises sodium ascorbate.

11. A process for producing microorganisms according to claim 1, wherein said microorganisms are lactic bacteria.

* * * * *